US010029237B2

(12) United States Patent
Cabiac et al.

(10) Patent No.: US 10,029,237 B2
(45) Date of Patent: Jul. 24, 2018

(54) CATALYST COMPRISING DISPERSED GOLD AND PALLADIUM, AND ITS USE IN SELECTIVE HYDROGENATION

(71) Applicant: IFP Energies nouvelles, Rueil-Malmaison (FR)

(72) Inventors: Amandine Cabiac, Givors (FR); Antoine Hugon, Givors (FR)

(73) Assignee: IFP Energies nouvelles, Rueil-Malmaison (FR)

(*) Notice: Subject to any disclaimer, the term of this patent is extended or adjusted under 35 U.S.C. 154(b) by 0 days.

(21) Appl. No.: 15/555,096

(22) PCT Filed: Feb. 9, 2016

(86) PCT No.: PCT/EP2016/052695
§ 371 (c)(1),
(2) Date: Sep. 1, 2017

(87) PCT Pub. No.: WO2016/139033
PCT Pub. Date: Sep. 9, 2016

(65) Prior Publication Data
US 2018/0036717 A1    Feb. 8, 2018

(30) Foreign Application Priority Data
Mar. 5, 2015 (FR) .................... 15 51872

(51) Int. Cl.
*B01J 21/04* (2006.01)
*B01J 21/06* (2006.01)
*B01J 21/08* (2006.01)
*B01J 21/10* (2006.01)
*B01J 21/12* (2006.01)
*B01J 23/10* (2006.01)
*B01J 23/44* (2006.01)
*B01J 23/52* (2006.01)
*B01J 23/63* (2006.01)
*B01J 35/00* (2006.01)
*B01J 35/02* (2006.01)
*B01J 37/02* (2006.01)
*C07C 5/09* (2006.01)
*C10G 45/40* (2006.01)

(52) U.S. Cl.
CPC .............. *B01J 23/52* (2013.01); *B01J 23/44* (2013.01); *B01J 35/006* (2013.01); *B01J 35/008* (2013.01); *B01J 35/0066* (2013.01); *B01J 35/0093* (2013.01); *B01J 35/023* (2013.01); *B01J 37/024* (2013.01); *B01J 37/0211* (2013.01); *C07C 5/09* (2013.01); *C10G 45/40* (2013.01); *C07C 2523/44* (2013.01); *C07C 2523/52* (2013.01); *C10G 2400/20* (2013.01)

(58) Field of Classification Search
CPC ........ B01J 21/04; B01J 21/063; B01J 21/066; B01J 21/08; B01J 21/10; B01J 21/12; B01J 23/10; B01J 23/44; B01J 23/52; B01J 23/63; B01J 35/006; B01J 35/0066; B01J 35/008; B01J 35/0093; B01J 35/023; B01J 37/0211; B01J 37/024; C07C 5/09; C10G 45/40
See application file for complete search history.

(56) References Cited

U.S. PATENT DOCUMENTS

| 6,509,292 | B1 | 1/2003 | Blankenship |
| 7,744,645 | B2* | 6/2010 | Thornton ................ A61L 31/10 623/1.42 |
| 7,998,247 | B2* | 8/2011 | Saukaitis ........... B01D 67/0046 422/211 |
| 8,338,327 | B2* | 12/2012 | Kadowaki ................ B01J 23/60 502/326 |
| 8,721,773 | B2* | 5/2014 | Perkins, II ........... B01D 53/228 427/270 |
| 2010/0010278 | A1 | 1/2010 | Boyer |
| 2010/0221167 | A1* | 9/2010 | Saukaitis ........... B01D 67/0046 423/248 |
| 2014/0039218 | A1* | 2/2014 | Dellamorte ............. C07C 51/25 560/261 |
| 2017/0101363 | A1* | 4/2017 | Dellamorte ............. C07C 67/04 |

FOREIGN PATENT DOCUMENTS

FR      2347095 A    4/1977
FR      2932177 A1   12/2009

OTHER PUBLICATIONS

International Search Report PCT/EP2016/052695 dated Apr. 12, 2016.
Pavani Malla: "Designing Supported Palladium-on-Gold Bimetallic Nano-Catalysts for Controlled Hydrogenation of Acetylene in Large Excess of Ethylene", Aug. 31, 2014 (Aug. 31, 2014), XP055241153, Retrieved from the Internet <<URL:http://dmc.tamuc.edu/cdm/ref/collection/p15778coll7/d/295>> [retrieved on Jan. 13, 2016].

* cited by examiner

*Primary Examiner* — Cam N. Nguyen
(74) *Attorney, Agent, or Firm* — Millen, White, Zelano and Branigan, P.C.

(57) ABSTRACT

A catalyst comprising gold, palladium, and a porous support, in the form of at least one grain, in which:
  the gold content in the catalyst is in the range 0.5% to 3% by weight with respect to the total weight of catalyst;
  the mean particle size of the gold, estimated by transmission electron microscopy (TEM), is in the range 0.5 nm to 5 nm;
  the gold is distributed homogeneously in the porous support;
  at least 80% by weight of the palladium is distributed in an eggshell at the periphery of the porous support;
  the gold/palladium molar ratio is more than 2.

15 Claims, No Drawings

CATALYST COMPRISING DISPERSED GOLD AND PALLADIUM, AND ITS USE IN SELECTIVE HYDROGENATION

TECHNICAL FIELD

The present invention relates to the field of heterogeneous catalysts in particular, and more particularly to supported catalysts comprising palladium and gold. The aim of the invention is to propose a catalyst, in particular for selective hydrogenation, as well as a mode of preparation of this catalyst.

PRIOR ART

The selective hydrogenation process can be used to transform the polyunsaturated compounds of oil cuts by conversion of the most unsaturated compounds into the corresponding alkenes, avoiding total saturation and thus the formation of the corresponding alkanes. The selective hydrogenation catalysts are often based on palladium, in the form of small metallic particles deposited on a support which may be a refractory oxide. The palladium content and the size of the palladium particles form a part of the criteria which are important to the activity and selectivity of the catalysts.

Catalysts based on palladium are widely used in reactions for the selective hydrogenation of light C2-C4 cuts. Typically, the palladium is distributed in a shell at the periphery of the catalyst (an eggshell catalyst). Recent years have seen the introduction of bimetallic catalysts which can provide a substantial gain in activity, but more especially in selectivity in the hydrogenation of acetylenes and diolefins. Typically, the element added to palladium is silver or gold.

The document US2006/025302 discloses a catalyst for the selective hydrogenation of acetylene and diolefins, comprising palladium, in a content in the range 0.01% to 0.1% by weight with respect to the total catalyst weight, and a metal from group IB, in a content in the range 0.005% to 0.06% by weight with respect to the total catalyst weight. The metal is preferably silver. The palladium is distributed in a manner such that 90% of the palladium introduced into the catalyst is in an eggshell of less than 250 µm.

The document U.S. Pat. No. 6,509,292 discloses a catalyst for the selective hydrogenation of acetylene, comprising palladium in a content of 0.001% to 0.028% by weight with respect to the total weight of catalyst and gold in a content of 0.18% to 1% by weight with respect to the total weight of catalyst. The gold/palladium ratio is in the range 6:1 to 50:1.

The palladium is distributed in a manner such that 90% of the metal is in an eggshell of less than 250 µm.

The document U.S. Pat. No. 6,350,717 describes a catalyst comprising at least one metal belonging to metals from column 10 in accordance with the IUPAC classification (for example palladium) and at least one metal belonging to metals from column 11 (for example gold) on a support formed from aluminium oxide (alumina), the metal belonging to column 10 essentially being concentrated at the surface of the support, and the metal belonging to column 11 being distributed essentially uniformly throughout the volume of the catalyst, the weight ratio between the metal from group 11 and the metal from group 10 not exceeding 1.95.

More particularly, these types of catalysts are used for the selective hydrogenation of light C2-C4 cuts at the head of the reactor (in a front end configuration). This configuration is characterized by the presence in the feed of a large excess of hydrogen and a variable quantity of carbon monoxide of between approximately 100 ppm mol and 2000 ppm mol. The carbon monoxide (CO) becomes partially adsorbed on the palladium. When the CO content increases or reduces in a C2-C4 feed, the activity of the selective hydrogenation catalysts, in particular of catalysts containing palladium, is modified.

The Applicant has established that it is possible to provide a supported catalyst based on palladium and gold, the gold and the palladium being mainly in the form of independent particles (i.e. the quantity of palladium-gold alloy is minor), the gold being in the form of small particles distributed in a homogeneous manner in the support, the palladium being distributed in an eggshell at the periphery of the support, to improve the stability of said catalyst towards changes in the concentration of CO in the feed. Furthermore, the stability of the catalyst in accordance with the invention is favoured by the presence of a large number of metallic gold sites, obtained for catalysts containing a large quantity by weight of gold; the gold is dispersed on a nanometric scale within the support.

Aims of the Invention

In a first aspect, the invention concerns a catalyst comprising gold, palladium, and a porous support, in the form of at least one grain, in which:

the gold content in the catalyst is in the range 0.5% to 3% by weight with respect to the total weight of catalyst;
the mean particle size of the gold, estimated by transmission electron microscopy (TEM), is in the range 0.5 nm to 5 nm;
the gold is distributed homogeneously in said porous support;
at least 80% by weight of the palladium is distributed in an eggshell at the periphery of said porous support;
the gold/palladium molar ratio is more than 2.

Preferably, the mean particle size of the gold, estimated by transmission electron microscopy, is in the range 0.5 nm to 3 nm.

Advantageously, the metallic dispersion D of the gold is in the range 30% to 100%.

Preferably, the palladium content is in the range 0.01% to 0.6% by weight with respect to the total weight of catalyst.

Advantageously, the thickness of said eggshell at the periphery of the porous support is less than 300 µm.

In another aspect, the invention concerns a process for the preparation of a catalyst in accordance with the invention comprising gold, palladium, and a porous support, in the form of at least one grain, said process comprising the following steps:

a step termed step 1, in which the palladium is introduced onto the support, comprising the following steps:
1a) preparing an aqueous solution of palladium oxide or palladium hydroxide;
1b) impregnating said solution onto at least one grain of porous support;
1c) maturing the impregnated porous support obtained in step 1b) in order to obtain a catalyst precursor;
1d) drying the catalyst precursor obtained in step 1c) at a temperature in the range 50° C. to 250° C.;
1e) calcining the catalyst precursor obtained in step 1d) at a temperature in the range 250° C. to 900° C.;
a step termed step 2, in which gold is introduced onto the support, comprising the following steps:
2a) preparing an aqueous solution containing a precursor of gold;

2b) impregnating said porous support with said solution obtained in step 2a);

2c) maturing the impregnated porous support obtained in step 2b) in order to obtain a catalyst precursor;

2d) bringing the catalyst precursor obtained in step 2c) into contact with a solution containing urea;

2e) drying the catalyst precursor obtained in step 2d) at a temperature in the range 50° C. to 300° C.

Preferably, in step 1a), a colloidal suspension of palladium oxide or palladium hydroxide is prepared in an aqueous phase.

Advantageously, dry impregnation is carried out in step 1b) and/or 2b).

Advantageously, the maturation step 1c) and/or 2c) is carried out for a period in the range 0.5 to 40 hours.

Preferably, between step 2c) and step 2d), a step for drying said catalyst precursor obtained in step 2c) is carried out at a temperature in the range 50° C. to 300° C.

Advantageously, the volume of the aqueous solution containing urea prepared in step 2d) is in the range 0.9 to 20 times the total pore volume of the shaped porous support.

Preferably, the urea/gold molar ratio is in the range 1 to 1000.

Preferably, a step 2o is also carried out, in which the dried catalyst obtained from step 2e) undergoes a reduction treatment by contact with a reducing gas.

Advantageously, the reduction step 2f) is carried out at a temperature in the range 40° C. to 500° C.

In another aspect, the invention concerns a process for the selective hydrogenation of a C2-C4 cut with a catalyst in accordance with the invention or prepared in accordance with the process of the invention, in which the temperature is in the range 0° C. to 500° C., the pressure is in the range 0.1 to 20 MPa, the hourly space velocity is in the range 0.1 to 50 $h^{-1}$ for a liquid feed, and in the range 500 to 30 000 $h^{-1}$ for a gaseous feed.

DETAILED DESCRIPTION OF THE INVENTION

The groups of chemical elements provided below are in accordance with the CAS classification (CRC Handbook of Chemistry and Physics, published by CRC press, Editor-in-Chief D. R. Lide, 81st edition, 2000-2001). As an example, the group IB in the CAS classification corresponds to metals from column 11 of the new IUPAC classification.

Catalyst

The invention concerns a catalyst comprising a porous support in the form of at least one grain, gold and palladium, in which:

the gold content in the catalyst is in the range 0.1% to 5% by weight with respect to the total weight of catalyst, preferably in the range 0.2% to 4% by weight, and more preferably in the range 0.3% to 3% by weight, and yet more preferably in the range 0.5% to 3% by weight;

the mean particle size of the gold, estimated by transmission electron microscopy (TEM), is in the range 0.5 nm to 5 nm, preferably less than 4 nm, and more preferably less than 3.5 nm, and yet more preferably less than 3 nm;

the gold is distributed homogeneously in said porous support;

at least 80% by weight of the palladium is distributed in an eggshell at the periphery of said porous support;

the gold/palladium molar ratio is more than 2, preferably more than 4, and more preferably more than 5.

In accordance with the invention, the term "grain" means the shaped porous support.

Advantageously, the thickness of said eggshell at the periphery of the porous support is less than 300 µm, preferably less than 250 µm.

Advantageously, the palladium content is in the range 0.01% to 0.6% by weight with respect to the total weight of catalyst, preferably in the range 0.01% to 0.3% by weight, and more preferably in the range 0.03% to 0.3% by weight; yet more preferably in the range 0.035% to 0.2% by weight, and even more preferably in the range 0.04% to 0.2% by weight.

The residual chlorine content is less than 200 ppm by weight with respect to the total weight of catalyst, preferably less than 100 ppm by weight, and more preferably less than 50 ppm by weight.

The gold is distributed homogeneously in the porous support with a coefficient R (described below) in the range 0.8 to 1.2.

The dispersion D (described below) for the gold, i.e. the quantity of superficial gold compared with the total gold introduced, is in the range 30% to 100%, preferably in the range 35% to 100%, and highly preferably in the range 38% to 100%.

The catalyst may also comprise an element from group IB (other than gold), preferably selected from silver and copper. Preferably, the element from group IB is silver. The quantity of the element from group IB is in the range 0.01% to 0.3% by weight with respect to the total weight of catalyst, preferably in the range 0.015% to 0.2% by weight.

The catalyst may comprise at least one metal selected from the group constituted by alkalis and alkaline-earths. The quantity of metal selected from the group constituted by the alkalis and the alkaline-earths is advantageously in the range 0.02% to 0.5% by weight with respect to the total catalyst weight.

The alkali metal is generally selected from the group constituted by lithium, sodium, potassium, rubidium and caesium, preferably by lithium, sodium and potassium, and more preferably by sodium and potassium.

The alkaline-earth metal is generally selected from the group constituted by magnesium, calcium, strontium and barium, preferably by magnesium and calcium, and more preferably by magnesium.

The alkali metal, when it is present, is distributed homogeneously in the support with a coefficient R (described below) in the range 0.8 to 1.2.

The alkaline-earth metal, when it is present, is distributed homogeneously in the support with a coefficient R (described below) in the range 0.8 to 1.2.

The porous support is selected from oxides of magnesium, aluminium, silicon, zirconium, thorium, titanium or cerium, used alone or as a mixture thereof. Preferably, the support is an oxide of aluminium (alumina) or of silicon (silica). More preferably, the support is alumina. The alumina may be present in any of the possible crystallographic forms: alpha, delta, theta, chi, gamma, etc, alone or as a mixture. Preferably, the support is selected from alpha, delta and theta alumina. More preferably, alpha alumina is selected.

The specific surface area of the porous support is in the range 1 to 300 $m^2/g$, preferably in the range 2 to 200 $m^2/g$, and more preferably in the range 3 to 150 $m^2/g$. The BET specific surface area is measured by nitrogen physisorption. The BET specific surface area is measured by nitrogen physisorption in accordance with the ASTM standard D3663-03 as described by Rouquerol F.; Rouquerol J.;

Singh K. in "Adsorption by Powders & Porous Solids: Principle, methodology and applications", Academic Press, 1999.

The total pore volume of the support is in the range 0.1 to 1.5 cm³/g, preferably in the range 0.2 to 1.4 cm³/g, and yet more preferably in the range 0.25 to 1.3 cm³/g. The total pore volume is measured by mercury porosimetry in accordance with the ASTM standard D4284-92, with a wetting angle of 140°, for example using an Autopore® III model instrument from Microméritics®.

In accordance with the invention, the grain of the porous support is in the form of beads, trilobes, extrudates, pellets or irregular and non-spherical agglomerates the specific shape of which may result from a crushing step. Highly advantageously, said support grain is in the form of beads or extrudates. Yet more advantageously, said support grain is in the form of beads. The grain size is in the range 1 mm to 10 mm, preferably in the range 2 to 8 mm.

The catalyst of the present invention may be characterized by several parameters which will be described below, in particular:
- the coefficient R, which expresses the homogeneous distribution of the gold in a grain of porous support;
- the thickness of the palladium eggshell formed at the periphery of the grain of porous support;
- the metallic dispersion D, which can be used to deduce the mean size of the metallic gold particles.

Metallic Dispersion D of Particles

The particle dispersion is a dimensionless number, often expressed as a %. The dispersion becomes larger as the particles become smaller. It is defined in the publication by R. Van Hardeveld and F. Hartog, "*The statistics of surface atoms and surface sites on metal crystals*", Surface Science 15, 1969, 189-230.

Definition of Coefficient R

The distribution profiles for the elements in the grains of catalyst are obtained by Castaing microprobe. At least 30 analysis points are recorded along the diameter of the bead or extrudate, in a proportion of about ten points on the eggshell of an active element (in this case gold) and about ten points at the centre of the grain. This thereby produces the distribution profile $c(x)$ for $x \in [-r;+r]$, where c is the local concentration of the element, r is the radius of the bead or extrudate and x is the position of the analysis point along the diameter of the grain with respect to the centre of that grain.

The distribution of the elements is characterized by a dimensionless coefficient R which weights the local concentration by a weight which increases as a function of the position on the diameter. By definition:

$$R = \int_{-r}^{r} c(x)x^2 dx \bigg/ \frac{r^2}{3}\int_{-r}^{r} c(x)dx$$

Thus, an element with a uniform concentration has a coefficient R equal to 1, an element deposited in a domed profile (concentration at the core higher than the concentration at the edges of the support) has a coefficient of more than 1 and an element distributed in an eggshell profile (concentration at edges higher than the concentration at the core of the support) has a coefficient of less than 1. The analysis by Castaing microprobe provides values for the concentrations for a finite number of values of x, and so R is evaluated numerically using integration methods which are well known to the skilled person. Preferably, R is determined using the trapezium method.

The distribution of the gold is defined as being homogeneous when the distribution coefficient R as defined above is in the range 0.8 to 1.2.

The distribution of the alkali element is defined as being homogeneous when the distribution coefficient R as defined above is in the range 0.8 to 1.2.

The distribution of the alkaline-earth element is defined as being homogeneous when the distribution coefficient R as defined above is in the range 0.8 to 1.2.

Definition of Eggshell Thickness of Palladium

In order to analyse the distribution of the metallic phase on the support, an eggshell thickness is measured by Castaing microprobe (or electronic microprobe microanalysis). The equipment used is a CAMECA XS100 equipped with four crystal monochromators allowing four elements to be analysed simultaneously. The Castaing microprobe analysis technique consists of detecting the X rays emitted by a solid after excitation of its elements with a beam of high energy electrons. For the purposes of this characterization, the beads of catalyst are coated with epoxy resin dots. These dots are polished until they reach the section which is the diameter of the beads, then metallized by depositing carbon using a metallic evaporator. The electronic probe is swept along the diameter of five beads in order to obtain the mean distribution profile for the constituent elements of the solids.

When the palladium is distributed as an eggshell, its local concentration generally reduces gradually when it is measured starting from the edge of the catalytic grain towards the interior. A distance from the edge of the grain, at which the local palladium concentration becomes zero, can often not be determined accurately and reproducibly. In order to measure an eggshell thickness which is significant for the majority of palladium particles, the eggshell thickness is defined as the distance to the edge of the grain containing 80% of the element.

In order to measure an eggshell thickness which is significant for the majority of palladium particles, the eggshell thickness may alternatively be defined as the distance to the edge of the grain containing 80% by weight of palladium. Starting from the distribution profile ($c(x)$) obtained by the Castaing microprobe, it is possible to calculate the cumulative quantity $Q(y)$ of palladium in the grain is calculated as a function of the distance y to the edge of a grain with radius r.

For a bead:

$$Q(y) = \int_{-r}^{-y} c(x) 4\pi \cdot x^2 dx + \int_{y}^{r} c(x) 4\pi \cdot x^2 dx$$

For an extrudate:

$$Q(y) = \int_{-r}^{-y} c(x) 2\pi \cdot x dx + \int_{y}^{r} c(x) 2\pi \cdot x dx$$

$Q(r)$ thus corresponds to the total quantity of the element in the grain. The following equation is then solved numerically for y:

$$\frac{Q(y)}{Q(r)} = 0.8$$

Since c is a strictly positive function, then Q is a strictly increasing function and this equation has a single solution which is the thickness of the eggshell.

Catalyst Preparation Process

In general, the catalyst preparation process comprises the following steps:

a first step, termed step 1, in which palladium is introduced onto at least one grain of porous support, the palladium being deposited using any method known to the person skilled in the art, in a manner such as to obtain an eggshell of less than 300 μm, followed by drying and calcining;

a second step, termed step 2, in which the gold is introduced.

It is important to emphasize that the preparation process is carried out in two distinct steps including a step for intermediate calcining between the two metal deposition steps.

Steps 1 and 2 may be carried out in any order. Preferably, step 1 is carried out before step 2. If step 2 is carried out before step 1, the reduction step 2σ is necessary.

Step 1 consists of preparing a porous support impregnated by impregnating palladium onto at least one grain of porous support in a manner such that the palladium is distributed in an eggshell at the periphery of said support grain, the thickness of said eggshell being less than 250 μm. The palladium solution may be deposited on the support using any of the techniques known to the person skilled in the art. Preferably, the palladium solution is deposited using the colloidal method.

Preferably, step 1) comprises the following steps:

1a) preparing a solution containing a precursor of palladium, preferably a colloidal suspension, of palladium oxide or palladium hydroxide in an aqueous phase;

1b) impregnating said solution onto at least one grain of porous support;

1c) maturing the impregnated porous support obtained in step 1b) in order to obtain a catalyst precursor;

1d) drying the catalyst precursor obtained in step 1c) at a temperature in the range 50° C. to 250° C.;

1e) calcining the catalyst precursor obtained in step 1d) at a temperature in the range 250° C. to 900° C.

Step 2) comprises the following steps:

2a) preparing an aqueous solution containing a precursor of gold;

2b) impregnating said porous support with said solution obtained in step 2a);

2c) maturing the impregnated porous support obtained in step 2b) in order to obtain a catalyst precursor;

2d) bringing the catalyst precursor obtained in step 2c) into contact with a solution containing urea;

2e) drying the catalyst precursor obtained in step 2d) at a temperature in the range 50° C. to 300° C., in air;

2f) optionally, the dried catalyst obtained from step 2e) undergoes a reduction treatment by contact with a reducing gas.

In accordance with the invention, step 2) does not include a non-reducing oxidizing or neutral heat treatment of the catalyst precursor in order to avoid the formation of coarse particles of gold (i.e. larger than 5 nm).

The various steps 1 and 2 are detailed below.

An optional step for drying the precursor obtained in step 2c) may be carried out by drying said precursor at a temperature in the range 50° C. to 300° C.

An optional step for depositing a metal from group IB (other than gold), preferably silver or copper, may also be carried out between steps 1 and 2 or simultaneously with step 1.

The catalyst may comprise at least one metal selected from the group constituted by alkalis and alkaline-earths. The alkali/alkaline-earth addition may be introduced separately before, during or after any steps for depositing palladium, optionally after depositing the metal from group IB (other than gold).

Step 2 is always preceded by an oxidizing heat treatment (calcining). No calcining is carried out after step 2.

Step 1: Depositing Palladium

Step 1a) Preparation of a Colloidal Suspension of Palladium Oxide or Palladium Hydroxide in an Aqueous Phase The colloidal suspension is generally obtained by hydrolysis of the palladium cation in an aqueous medium, which results in the formation of particles of palladium oxide or hydroxide in suspension.

The aqueous solution of alkali hydroxide or alkaline-earth hydroxide is generally selected from the group constituted by aqueous solutions of sodium hydroxide and aqueous solutions of magnesium hydroxide. Preferably, the aqueous solution is an aqueous solution of sodium hydroxide.

The palladium precursor salt is generally selected from the group constituted by palladium chloride, palladium nitrate and palladium sulphate. Highly preferably, the palladium precursor salt is palladium nitrate.

Typically, the aqueous solution comprising at least one precursor salt of palladium [also known here as solution (II)] is placed in a suitable apparatus, followed by the aqueous solution comprising at least one alkali or alkaline-earth hydroxide [also termed solution (I) here]. Alternatively, the solutions (I) and (II) may be poured into the apparatus simultaneously. Preferably, the aqueous solution (II) followed by the aqueous solution (I) is poured into the apparatus.

The colloidal suspension generally remains in the apparatus for a residence time in the range 0 to 20 hours.

The concentrations of solution (I) and (II) are generally selected in order to obtain a pH for the colloidal solution in the range 1.0 to 3.5. Thus, the pH of the colloidal suspension may be modified during this residence time by adding quantities of acid or base which are compatible with the stability of the colloidal suspension.

In general, the preparation temperature is in the range 5° C. to 40° C., preferably in the range 15° C. to 35° C.

The concentration of palladium is preferably in the range 5 to 150 millimoles per liter (mmol/L), more preferably in the range 8 to 80 millimoles per liter.

Step 1b) Depositing the Colloidal Suspension Prepared in Step 1a) by Impregnation onto a Support, Preferably onto Alumina The colloidal suspension prepared in step 1a) is then impregnated onto a support.

The support may optionally undergo a set of treatments prior to the impregnation step, such as calcining or hydration steps. The support may also already comprise one or more metallic elements prior to impregnation of the colloidal suspension. The metallic elements may also be introduced into the colloidal suspension. These metallic elements may be introduced either using conventional techniques, or using the process in accordance with the present invention.

The colloidal suspension is preferably poured onto the support. This process may be carried out either batchwise, i.e. the step for preparing the colloidal suspension precedes the step for impregnation onto the support and the essential part of the colloidal suspension is sent all at once to the impregnation step, or continuously, i.e. the product obtained in step 1a) is sent continuously after adjusting the residence time for the colloidal suspension in step 1b).

An example of a continuous process which may be cited is a process in which solutions 1 and 2 are simultaneously poured into a tank which continuously overflows into a zone comprising the support to be impregnated.

Step 1c) Maturing the Support Impregnated During Step b) for a Period in the Range 0.5 to 40 Hours After impregnation, the impregnated porous support is generally matured for 0.5 to 40 hours, preferably for 1 to 30 hours, preferably at ambient temperature.

Preferably, said maturation step is carried out in air, and preferably in moist air with a relative humidity in the range 20% to 100%, preferably in the range 70% to 100%.

Step 1d) Drying the Catalyst Precursor Obtained in Step c)

The catalyst precursor is generally dried in order to eliminate all or a portion of the water introduced during impregnation, preferably at a temperature in the range 50° C. to 250° C., more preferably in the range 70° C. to 200° C. The drying period is in the range 0.5 to 20 hours.

Drying is generally carried out in hydrocarbon combustion air, preferably methane, or in heated air comprising 0 to 80 grams of water per kg of combustion air, with an oxygen content in the range 5% to 25% by volume and a carbon dioxide content in the range 0 to 10% by volume.

Step 1e) Calcining Dried Catalyst Obtained in Step 1d) in Combustion Air

After drying, the catalyst is generally calcined in combustion air, preferably air from the combustion of methane comprising 40 to 80 grams of water per kg of combustion air, an oxygen content in the range 5% to 15% by volume and a $CO_2$ content in the range 4% to 10% by volume. The calcining temperature is generally in the range 250° C. to 900° C., preferably in the range from approximately 300° C. to approximately 500° C. The calcining period is generally in the range 0.5 hours to 5 hours.

In a variation, the catalyst may contain one or more promoter metals. The promoter metal or metals may be introduced during the preparation of the support, onto the pre-formed support, during step 1a) or at the end of steps 1b), 1c), 1d) or 1e).

Step 2: Depositing Gold

Step 2a) Preparation of an Impregnation Solution in Aqueous Phase

The solution is prepared by dissolving a gold precursor salt.

The precursor salt of gold used has an oxidation number for the metal of more than 0 and is soluble in aqueous solution. The gold precursor salt may be a halide, for example. It may preferably be selected from the group constituted by chlorides of gold such as gold trichloride, tetrachloroauric acid, sodium or potassium tetrachloraurate. Preferably, the precursor used is tetrachloroauric acid.

In general, the preparation temperature is in the range 5° C. to 40° C. and preferably in the range 15° C. to 35° C. The concentration of gold in the solution is preferably in the range 1 mmol/L to 1 mol/L, i.e. 0.2 g/L to 200 g/L.

Step 2b) Deposition of the Solution Prepared in Step 2a)

The solution prepared in step 2a) is then impregnated onto the porous support. The support may be impregnated by dry impregnation, excess impregnation or depleted impregnation, in static or dynamic mode. Dry impregnation is preferred. The impregnation may be carried out in one or more successive impregnation steps.

The dry impregnation step consists of bringing said porous support into contact with at least one solution containing at least one precursor of gold; the volume is equal to the pore volume of said support to be impregnated. This solution contains the metallic gold precursor in the concentration needed in order to obtain the desired final gold content on the catalyst.

The porous support has a specific surface area in the range 1 to 300 m$^2$/g, preferably in the range 2 to 200 m$^2$/g, and more preferably in the range 3 to 150 m$^2$/g.

The support may optionally undergo a series of treatments before the impregnation step, such as calcining or hydration steps.

Step 2c) Maturation of the Impregnated Support Obtained in Step 2b)

After impregnation, the impregnated porous support is generally matured for 0.5 to 40 hours, preferably for 1 to 30 hours, preferably at ambient temperature. Preferably, said maturation step is carried out in air and preferably in moist air with a relative humidity in the range 20% to 100%, preferably in the range 70% to 100%.

Optionally, the catalyst precursor may be dried in order to eliminate all or a portion of the water introduced during impregnation, preferably at a temperature in the range 50° C. to 300° C., more preferably in the range 70° C. to 250° C. The drying period is in the range 0.5 h to 20 h. Drying is generally carried out in hydrocarbon combustion air, preferably methane, or in heated air comprising 0 to 80 grams of water per kg of combustion air, with an oxygen content in the range 5% to 25% by volume and a carbon dioxide content in the range 0 to 10% by volume.

Step 2d) Treatment with Urea

The catalyst is brought into contact, with stirring, with an aqueous solution comprising at least urea.

The volume of the aqueous solution containing at least urea is in the range 0.9 to 20 times the pore volume of the shaped catalyst.

The molar urea/gold ratio is in the range 1 to 1000, preferably in the range 2 to 700, more preferably in the range 3 to 300.

In general, the temperature of the solution is kept constant and is in the range 5° C. to 120° C., and preferably in the range 15° C. to 100° C. The dwell time for said aqueous solution in the apparatus is in the range 0.5 to 20 hours.

The urea is diluted in an organic solvent, for example ethanol, and/or an aqueous solvent; preferably, the solvent is water.

The solution containing urea may also contain other organic compounds such as ammonia. Preferably, the solution contains only urea and water.

Filtration/Washing

Optionally, the catalyst precursor obtained in step d) may be filtered using any technique which is known to the person skilled in the art.

Optionally, the catalyst precursor is washed, preferably with water. The total volume of water engaged for the washing step(s) is in the range 1 to 30 times the catalytic volume engaged. Washing may be carried out in one or more steps. Washing the catalyst precursor means that the urea and chlorine present in the catalyst precursor can be eliminated.

The washing period is generally in the range 1 minute to 10 hours, preferably in the range 5 minutes to 8 hours, and more preferably in the range 10 minutes to 7 hours. Washing can be used to reduce the quantity of elemental chlorine which might be present in the catalyst precursor.

Step 2e) Drying of Catalyst Precursor Obtained in Step 2d)

The catalyst is generally dried in order to eliminate all or a portion of the water introduced during impregnation, preferably at a temperature in the range 50° C. to 300° C., more preferably in the range 70° C. to 250° C. The drying period is in the range 0.5 to 20 hours.

Drying is generally carried out in hydrocarbon combustion air, preferably methane, or in heated air comprising 0 to 80 grams of water per kilogram of combustion air, with an oxygen content in the range 5% to 25% by volume and a carbon dioxide content in the range 0 to 10% by volume.

Step 2f) Heat Treatment of the Dried Catalyst Obtained in Step 2e) in a Reducing Atmosphere Optionally, after drying, the catalyst is reduced. This step is preferably carried out in the presence of a reducing gas, either in situ, i.e. in the reactor where the catalytic transformation is carried out, or ex situ. In general, the reduction temperature is in the range 40° C. to 500° C., preferably in the range from approximately 100° C. to approximately 400° C.

The reduction is carried out in the presence of a reducing gas comprising in the range 25% by volume to 100% by volume of hydrogen, preferably 100% by volume of hydrogen. The hydrogen is optionally supplemented by a gas which is inert as regards reduction, preferably argon, nitrogen or methane. The reduction generally comprises a temperature ramp-up phase followed by a constant temperature stage.

The duration of the constant temperature stage for reduction is generally in the range 0.5 to 10 hours, preferably in the range 2 to 8 hours.

The HSV is generally in the range 150 to 3000, preferably in the range 300 to 1500 liters of reducing gas per hour and per liter of catalyst. The term "HSV" as used in the context of the present invention means the hourly space velocity, defined as the ratio between the volume flow rate of the feed to be treated and the volume of catalyst charged into the reactor. The hourly space velocity is expressed in $h^{-1}$.

In the embodiment in which step 2 is carried out before step 1, step 2f) is necessary.

Use of the Catalyst in Accordance with the Invention

The catalyst in accordance with the invention may be used in reactions for the hydrogenation of compounds comprising acetylene, diene and olefin functions.

In particular, the invention concerns bringing the catalyst in accordance with the invention into contact with a feed which is selected from the group constituted by steam cracking and/or catalytic cracking C2, C3 cuts, C4 cuts, C5 cuts and gasolines from steam cracking, also known as pyrolysis gasolines; preferably the feeds are C2, C3 or C4 cuts from steam cracking and/or catalytic cracking Depending on the arrangement of the units downstream of the steam cracking, the compositions of the feeds studied for selective hydrogenation will vary. The nature and the quantity of the hydrocarbons, the $H_2/HC$ ratio, the nature and the quantity of the impurities (sulphur, CO, $CO_2$) vary as a function of the type of configuration.

Selective hydrogenation at the head of the reactor (also known as selective hydrogenation in a "front end" configuration) is generally operated in the gas phase. The typical composition of the selective hydrogenation feeds in the "front end" configuration includes an acetylene content in the range 0.15% to 0.5%, an ethylene content in the range 20% to 50%, an ethane content in the range 5% to 15% and a hydrogen content in the range 5% to 20%, a methane content in the range 20% to 40%, and a CO content in the range 50 to 3000 ppm mol. Thus, there exists a very large excess of hydrogen with respect to the acetylene in the feeds under "front end" conditions. The CO contents can vary. CO is known to be adsorbed onto the metallic active sites of the catalyst, reducing its activity. A sudden reduction in CO will liberate sites for hydrogenation and thus result in overactivity and potentially in reactor runaway. In contrast, an increase in the CO content leads to a drop in the catalyst performance. Highly preferably, the catalyst is brought into contact with a feed which is a C2 or C2/C3 cut under "front end" conditions.

The operating conditions for selective hydrogenation under "front end" conditions are as follows: a temperature in the range 30° C. to 200° C., a pressure in the range 1.5 to 4.0 MPa and a hourly space velocity in the range 1000 $h^{-1}$ to 30000 $h^{-1}$.

EXAMPLES

The examples presented below are aimed at demonstrating the improvement in catalytic activity for selective hydrogenation. Examples 1 to 4 and 7 and 8 concern processes for the preparation of catalysts which are not in accordance with the invention, and Examples 5 and 6 concern a process for the preparation of a catalyst in accordance with the invention.

Example 9 concerns the application of these catalysts in a selective hydrogenation reaction. These examples are presented by way of illustration and do not in any way limit the scope of the invention.

Example 1: Preparation of a Catalyst C1: 0.06% by Weight Pd/δ-$Al_2O_3$ (Not in Accordance with the Invention)

This example demonstrates the preparation of a palladium on delta alumina catalyst.

A colloidal suspension of palladium oxide was prepared, with stirring at 25° C., by diluting 0.60 grams of a solution of palladium nitrate $Pd(NO_3)_2$ containing 8.5% by weight of palladium with 45 mL of demineralized water, then adding approximately 10 mL of a sodium hydroxide solution. The suspension was then diluted with demineralized water to a volume which corresponded to the pore volume of the alumina support. This solution was then impregnated onto 80 grams of an alumina with a specific surface area of 140 $m^2/g$ shaped into the form of 2-4 mm beads. A step for maturation of the impregnated support before drying for a period of 20 hours was carried out in air in a confined and moist medium. The solid obtained was dried in air for 2 hours at 120° C. The catalyst was then calcined in a stream of air for 2 hours at 450° C.

The catalyst C1 contained 0.06% by weight of palladium with respect to the total weight of the catalyst. Characterization of catalyst C1 by Castaing microprobe showed that 80% of the palladium was distributed over an eggshell with a thickness of less than 250 μm.

Example 2: Preparation of a Catalyst C2: 0.06% by Weight Pd/α-$Al_2O_3$ (Not in Accordance with the Invention)

This example demonstrates the preparation of a palladium on alpha alumina catalyst.

A colloidal suspension of Pd oxide was prepared, with stirring at 25° C., by diluting 0.60 grams of a solution of palladium nitrate $Pd(NO_3)_2$ containing 8.5% by weight of palladium with approximately 45 mL of demineralized water, then adding approximately 10 mL of a sodium hydroxide solution. The suspension was then diluted with demineralized water to a volume which corresponded to the pore volume of the alumina support. This solution was then impregnated onto 80 grams of an alumina with a specific surface area of 10 m$^2$/g shaped into the form of 2-4 mm beads. A step for maturation of the impregnated support before drying for a period of 20 hours was carried out in air in a confined and moist medium. The solid obtained was dried in air for 2 hours at 120° C. The catalyst was then calcined in a stream of air for 2 hours at 450° C.

The catalyst C2 contained 0.06% by weight of palladium with respect to the total weight of the catalyst. Characterization of catalyst C2 by Castaing microprobe showed that 80% of the Pd was distributed over an eggshell with a thickness of less than 250 µm.

Example 3: Preparation of a Catalyst C3: Pd (0.06% by Weight)+Au (2% by Weight)/δ-Al$_2$O$_3$ (Not in Accordance with the Invention)

This example demonstrates the conventional preparation of a catalyst comprising palladium and gold by dry impregnation only (and thus without washing with urea).

A stock solution with a concentration of 20 g/L (102 mmol/L) was prepared by diluting two grams of HAuCl$_4$.3H$_2$O with approximately 50 mL of demineralized water, with stirring at 25° C. A portion of the suspension was then impregnated onto 20 grams of catalyst C1. A maturation step for 20 h was carried out on the impregnated support before drying in air in a confined and moist medium. The solid obtained was dried in air for 2 h at 100° C. The catalyst was then reduced in a stream of hydrogen for 2 h at 300° C.

The catalyst C3 contained 2% by weight of gold, 1.4% by weight of chlorine and 0.06% by weight of palladium with respect to the total weight of catalyst. The Au/Pd weight ratio of the catalyst was 33.

Characterization of the catalyst by Castaing microprobe showed that the gold was distributed homogeneously with a distribution coefficient R (Au)=0.91.

Characterization of the catalyst by Castaing microprobe showed that the chlorine was distributed homogeneously with a distribution coefficient R(Cl)=0.89.

The mean size for the gold particles, measured by transmission electron microscopy, was 30 nm. The corresponding mean dispersion was 4%.

Characterization of the catalyst C3 by Castaing microprobe showed that 80% of the palladium was distributed over an eggshell with a thickness of less than 250 µm.

Example 4: Preparation of a Catalyst C4: Pd (0.06% by Weight)+Au (2% by Weight)/δ-Al$_2$O$_3$ (Not in Accordance with the Invention)

This example showed the preparation of a catalyst for which gold was introduced into the catalyst by deposition—precipitation, and in which the gold and urea were introduced simultaneously in solution as described, for example, in the document FR 2 932 177.

A suspension containing 20 grams of catalyst C1 shaped into beads and 150 mL of water were placed in a reactor and heated to 80° C. 20 mL of a 20 g/L (102 mmol/L) gold solution was introduced into the reactor. 12 grams of urea diluted in 20 mL of demineralized water was then added. The urea/gold molar ratio was 100. The suspension was stirred for 6 hours. The solid was filtered through a Buchner funnel then washed three times with 150 mL of water.

The solid obtained was dried in air for 2 hours at 100° C. The catalyst was then reduced in a stream of hydrogen for 2 hours at 300° C.

The catalyst C4 contained 1.7% by weight of gold, a chlorine content of less than 300 ppm by weight with respect to the total weight of the catalyst, and 0.06% by weight of palladium with respect to the total weight of the catalyst. The Au/Pd weight ratio of the catalyst was 28.

Characterization of the catalyst C4 by Castaing microprobe showed that the gold was distributed at the periphery of the catalyst with a distribution coefficient R (Au)=0.49.

The mean particle size for the gold, measured by transmission electron microscopy, was 4 nm.

The corresponding mean dispersion was 33%.

Characterization of the catalyst C4 by Castaing microprobe showed that 80% of the palladium was distributed over an eggshell with a thickness of less than 250 µm.

Example 5: Preparation of a Catalyst C5 in Accordance with the Invention

A stock solution with a concentration of 20 g/L (102 mmol/L) was prepared by diluting 2 grams of HAuCl$_4$.3H$_2$O with approximately 50 mL of demineralized water, with stirring at 25° C. A portion of the suspension was then impregnated onto 20 grams of catalyst C1 shaped into the form of 2-4 mm beads. A maturation step for 20 h was carried out on the impregnated support before drying in air in a confined and moist medium. The solid obtained was dried in air for 2 h at 100° C.

The catalyst was then impregnated with the pore volume of a solution of urea in a concentration of 80 g/L. The suspension was stirred at 70° C. for 4 hours. The urea/gold molar ratio was 13. The solid was then filtered and washed 4 times with 150 mL of water. The solid obtained was dried in air for 2 hours at 120° C. The catalyst was then reduced in a stream of hydrogen for 2 hours at 300° C.

The catalyst C5 contained 1.9% by weight of gold, a chlorine content of less than 0.03% by weight with respect to the total weight of the catalyst and 0.06% by weight of palladium with respect to the total weight of the catalyst. The Au/Pd weight ratio of the catalyst was 32.

Characterization of the catalyst by Castaing microprobe showed that the gold was distributed homogeneously with a distribution coefficient R (Au)=1.12.

The mean particle size for the gold, measured by transmission electron microscopy, was 2.6 nm. The corresponding mean dispersion was 44%.

The catalyst C5 contained 0.06% by weight of palladium. Characterization of the catalyst C5 by Castaing microprobe showed that 80% of the Pd was distributed over an eggshell with a thickness of less than 250 µm.

Example 6: Preparation of a Catalyst C6 in Accordance with the Invention

A stock solution with a concentration of 30 g/L (153 mmol/L) was prepared by diluting 2 grams of HAuCl$_4$.3H$_2$O with approximately 35 mL of demineralized water, with stirring at 25° C. A portion of the suspension was then impregnated onto 20 grams of catalyst C2 shaped into the form of beads. A maturation step for 20 h was carried out on the impregnated support before drying in air in a confined and moist medium. The solid obtained was dried in air for 2 h at 100° C.

The catalyst was then impregnated with a solution of urea in a concentration of 100 g/L. The suspension was stirred at 70° C. for 4 hours. The urea/gold molar ratio was 12.

The solid was then filtered and washed 4 times with 150 mL of water. The catalyst was then reduced in a stream of hydrogen for 2 hours at 300° C.

The catalyst C6 contained 1.7% by weight of gold, a chlorine content of less than 0.03% by weight with respect to the total weight of the catalyst and 0.06% by weight of palladium with respect to the total weight of the catalyst. The Au/Pd weight ratio of the catalyst was 26.

Characterization of the catalyst by Castaing microprobe showed that the gold was distributed homogeneously with a distribution coefficient R (Au)=0.95.

The mean particle size for the gold, measured by transmission electron microscopy, was 3.1 nm. The corresponding mean dispersion was 40%.

The catalyst C6 contained 0.06% by weight of palladium. Characterization of the catalyst C6 by Castaing microprobe showed that 80% of the palladium was distributed over an eggshell with a thickness of less than 250 μm.

Example 7: Preparation of a Catalyst C7: 0.02% by Weight Pd/α-Al$_2$O$_3$ (Not in Accordance with the Invention)

This example demonstrates a method for the preparation of a catalyst comprising palladium on alpha alumina.

then impregnated onto 20 grams of catalyst C7 shaped into the form of 2-4 mm beads. The solid obtained was calcined in air for 3 hours at 450° C.

The catalyst was then reduced in the aqueous phase in the presence of a sodium formate solution at 70° C. for 1 h. The catalyst was then washed with water at 70° C., then dried overnight at 120° C.

The catalyst C8 contained 0.8% by weight of gold and had a chlorine content of less than 0.01% by weight with respect to the total weight of the catalyst and 0.02% by weight of palladium with respect to the total weight of the catalyst. The Au/Pd weight ratio of the catalyst was 40.

Characterization of the catalyst by Castaing microprobe showed that the gold was distributed with a distribution coefficient R (Au)=0.90.

The mean particle size for the gold, measured by transmission electron microscopy, was 30 nm. The corresponding mean dispersion was 4%.

The catalyst C8 contained 0.02% by weight of palladium. Characterization of the catalyst C8 by Castaing microprobe showed that 80% of the palladium was distributed over an eggshell with a thickness of less than 250 μm.

Table 1 below summarizes the characteristics of the various catalysts C1 to C8

TABLE 1

| Catalyst | C1 | C2 | C3 | C4 | C5 | C6 | C7 | C8 |
|---|---|---|---|---|---|---|---|---|
| Support | δ-Al$_2$O$_3$ | α-Al$_2$O$_3$ | δ-Al$_2$O$_3$ | δ-Al$_2$O$_3$ | δ-Al$_2$O$_3$ | α-Al$_2$O$_3$ | α-Al$_2$O$_3$ | α-Al$_2$O$_3$ |
| R (gold) | / | / | 0.91 | 0.49 | 1.12 | 0.95 | / | 0.90 |
| Size of gold (nm) | / | / | 30 | 4 | 2.6 | 3.1 | / | 30 |
| Dispersion of gold (%) | / | / | 4 | 33 | 44 | 40 | / | 4 |
| Gold/Palladium | / | / | 33 | 28 | 32 | 26 | / | 40 |
| Pd eggshell (nm) | 80% (250 μm) | 80% (250 μm) | 80% (250 μm) | 80% (250 μm) | 80% (250 μm) | 80% (250 μm) | 80% (250 μm) | 80% (250 μm) |

A suspension of a Pd salt precursor was prepared, with stirring at 25° C., by diluting 0.20 grams of a solution of palladium nitrate Pd(NO$_3$)$_2$ containing 8.5% by weight of palladium with approximately 45 mL of demineralized water. The suspension was then diluted with demineralized water to a volume which corresponded to the pore volume of the alumina support. This solution was then impregnated onto 80 g of alpha alumina the specific surface area of which was 10 m$^2$/g, shaped into 2-4 mm beads. The solid obtained was dried in air for 2 h at 120° C. The catalyst was then calcined in a stream of air for 2 h at 450° C.

The catalyst C7 contained 0.02% by weight of palladium with respect to the total weight of the catalyst. Characterization of the catalyst C2 by Castaing microprobe showed that 80% of the Pd was distributed over an eggshell with a thickness of less than 250 μm.

Example 8: Preparation of a Catalyst C8: Pd (0.02% by Weight)+Au (0.8% by Weight)/α-Al$_2$O$_3$ (Not in Accordance with the Invention)

This example demonstrates the preparation of a catalyst comprising palladium and gold by dry impregnation (but without washing with urea) as described, for example, in the document U.S. Pat. No. 6,506,292.

A stock solution with a concentration of 20 g/L (102 mmol/L) was prepared by diluting one gram of HAuCl$_4$.3H$_2$O with approximately 25 mL of demineralized water, with stirring at 25° C. A portion of the solution was It will be observed that only a preparation combining an impregnation with a palladium precursor, an impregnation with a gold precursor, followed by a maturation step, and contact with urea by washing could produce a catalyst comprising particles of gold with small dimensions with a very good dispersion and which are distributed in a homogeneous manner through the grains of porous support, while obtaining a distribution of palladium in an eggshell at the periphery of said porous support.

Example 9: Use of Catalysts C1, C2, C3, C4, C5, C6 and C8 for the Selective Hydrogenation of the C2 Cut in the "Front End" Configuration A feed comprising 0.31% of acetylene, 40% of ethylene, 6% by weight of ethane, 30% of methane, 16% of hydrogen and a CO content of 250 ppm mol, with the complement being nitrogen, was treated with the catalysts C1, C2, C3, C4, C5, C6 and C8.

Before the reaction, the catalysts C1, C2, C3, C4, C5, C6 and C8 were activated in a stream of pure hydrogen at 160° C. for 2 hours. 5 mL of catalysts was placed in a tube reactor in downflow mode. The pressure of the reactor was maintained at 3 MPa. An hourly space velocity (GHSV) of 3000 h$^{-1}$ was applied. The composition of the feed and of the effluent were measured continuously at the reactor outlet by gas phase chromatography.

The performances were expressed as the temperature T1, defined as the temperature necessary to obtain an acetylene conversion of 98%. The temperatures T1 of the catalysts C1, C2, C3, C4, C5, C6 and C8 are reported in Table 2 (below).

The reactor temperature was kept constant at the temperature T1. The CO content in the feed was modified suddenly. The concentration of CO reduced from 250 ppm molar to 80 ppm molar. The CO content in the effluents was measured at the reactor outlet. The time "t" denotes the time necessary for the CO content measured at the reactor outlet to drop below 150 ppm molar. The values for t for the various catalysts are summarized in Table 2 (below).

TABLE 2

| Catalyst | Temperature (° C.) | Time "t" (in min) to obtain a CO content of less than 150 ppm molar |
|---|---|---|
| C1 (not in accordance with the invention) | 43 | <1 |
| C2 (not in accordance with the invention) | 51 | <1 |
| C3 (not in accordance with the invention) | 42 | 2 |
| C4 (not in accordance with the invention) | 47 | 4 |
| C5 (in accordance with the invention) | 50 | 9 |
| C6 (in accordance with the invention) | 55 | 8 |
| C8 (not in accordance with the invention) | 51 | 2 |

For the tests carried out with the monometallic $Pd/Al_2O_3$ catalysts C1 and C2 (not in accordance with the invention), the time necessary to observe a CO content in the effluents of 150 ppm was very short, less than one minute.

When gold was present in the catalyst, the period was increased.

For the catalysts C3, C4 and C8 which were not in accordance with the inventions, the period was between 2 and 4 minutes respectively.

The catalysts C5 and C6 which were in accordance with the invention and contained gold dispersed on a nanometric scale and distributed homogeneously in the catalyst support and contained palladium distributed in an eggshell at the periphery of the porous support were those for which a CO content of less than 150 ppm mol was observed with the longest period. The catalysts in accordance with the invention thus act as a buffer for CO and prevent sudden variations in CO in contact with said catalysts. They can thus be used to provide improved catalytic performances for the selective hydrogenation of the C2 cut in the "front end" configuration.

The invention claimed is:

1. A catalyst comprising gold, palladium, and a porous support, in the form of at least one grain, wherein:
    the gold content in the catalyst is in the range 0.5% to 3% by weight with respect to the total weight of catalyst;
    the mean particle size of the gold, estimated by transmission electron microscopy (TEM), is in the range 0.5 nm to 5 nm;
    the gold is distributed homogeneously in said porous support;
    at least 80% by weight of the palladium is distributed in an eggshell at the periphery of said porous support;
    the gold/palladium molar ratio is more than 2.

2. The catalyst as claimed in claim 1, wherein the mean particle size of the gold, estimated by transmission electron microscopy, is in the range 0.5 nm to 3 nm.

3. The catalyst as claimed in claim 1, wherein the metallic dispersion D of the gold is in the range 30% to 100%.

4. The catalyst as claimed in claim 1, wherein the palladium content is in the range 0.01% to 0.6% by weight with respect to the total weight of catalyst.

5. The catalyst as claimed in claim 1, wherein the thickness of said eggshell at the periphery of the porous support is less than 300 μm.

6. A process for the preparation of a catalyst as claimed in claim 1, comprising gold, palladium, and a porous support, in the form of at least one grain, said process comprising:
    1) introducing the palladium onto the support, by:
        1a) preparing an aqueous solution of palladium oxide or palladium hydroxide;
        1b) impregnating said solution onto at least one grain of porous support;
        1c) maturing the impregnated porous support obtained in 1b) in order to obtain a catalyst precursor;
        1d) drying the catalyst precursor obtained in 1c) at a temperature in the range 50° C. to 250° C.;
        1e) calcining the catalyst precursor obtained in 1d) at a temperature in the range 250° C. to 900° C.;
    2) introducing gold onto the support, comprising:
        2a) preparing an aqueous solution containing a precursor of gold;
        2b) impregnating said porous support with said solution obtained in 2a);
        2c) maturing the impregnated porous support obtained in 2b) in order to obtain a catalyst precursor;
        2d) bringing the catalyst precursor obtained in 2c) into contact with a solution containing urea;
        2e) drying the catalyst precursor obtained in 2d) at a temperature in the range 50° C. to 300° C.

7. The process as claimed in claim 6 wherein, in 1a), a colloidal suspension of palladium oxide or palladium hydroxide is prepared in an aqueous phase.

8. The process as claimed in claim 6, wherein dry impregnation is carried out in 1b) and/or 2b).

9. The process as claimed in claim 6, wherein maturation 1c) and/or 2c) is carried out for a period in the range 0.5 to 40 hours.

10. The process as claimed in claim 6, wherein between 2c) and 2d), drying of the catalyst precursor obtained in 2c) is carried out at a temperature in the range 50° C. to 300° C.

11. The process as claimed in claim 6, wherein the volume of the aqueous solution containing urea prepared in 2d) is in the range 0.9 to 20 times the total pore volume of the shaped porous support.

12. The process as claimed in claim 6, wherein the urea/gold molar ratio is in the range 1 to 1000.

13. The process as claimed in claim 6, comprising 2f) reducing the dried catalyst obtained from 2e) by contact with a reducing gas.

14. The process as claimed in claim 13, wherein reduction 2f) is carried out at a temperature in the range 40° C. to 500° C.

15. A process for the selective hydrogenation of a C2-C4 cut comprising contacting said C2-C4 cut with a catalyst in accordance with claim 1, at a temperature in the range 0° C. to 500° C., a pressure in the range 0.1 to 20 MPa, and an hourly space velocity in the range 0.1 to 50 $h^{-1}$ for a liquid feed, and in the range 500 to 30 000 $h^{-1}$ for a gaseous feed.

* * * * *